US00PP35614P2

(12) United States Plant Patent
van den Hoogen

(10) Patent No.: US PP35,614 P2
(45) Date of Patent: Jan. 30, 2024

(54) ***VERONICA* PLANT NAMED 'ALLVBABY'**

(50) Latin Name: ***Veronica longifolia* X *Veronica spicata***

Varietal Denomination: 'Allvbaby'

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 351 days.

(21) Appl. No.: 17/844,662

(22) Filed: Jun. 20, 2022

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Veronica* plant named 'Allvbaby', characterized by its relatively compact and broadly upright plant habit; moderately vigorous growth habit; freely branching habit; medium green-colored leaves; freely flowering habit; dense inflorescences with numerous violet-colored flowers; and good performance as a garden plant.

2 Drawing Sheets

Figure 1:
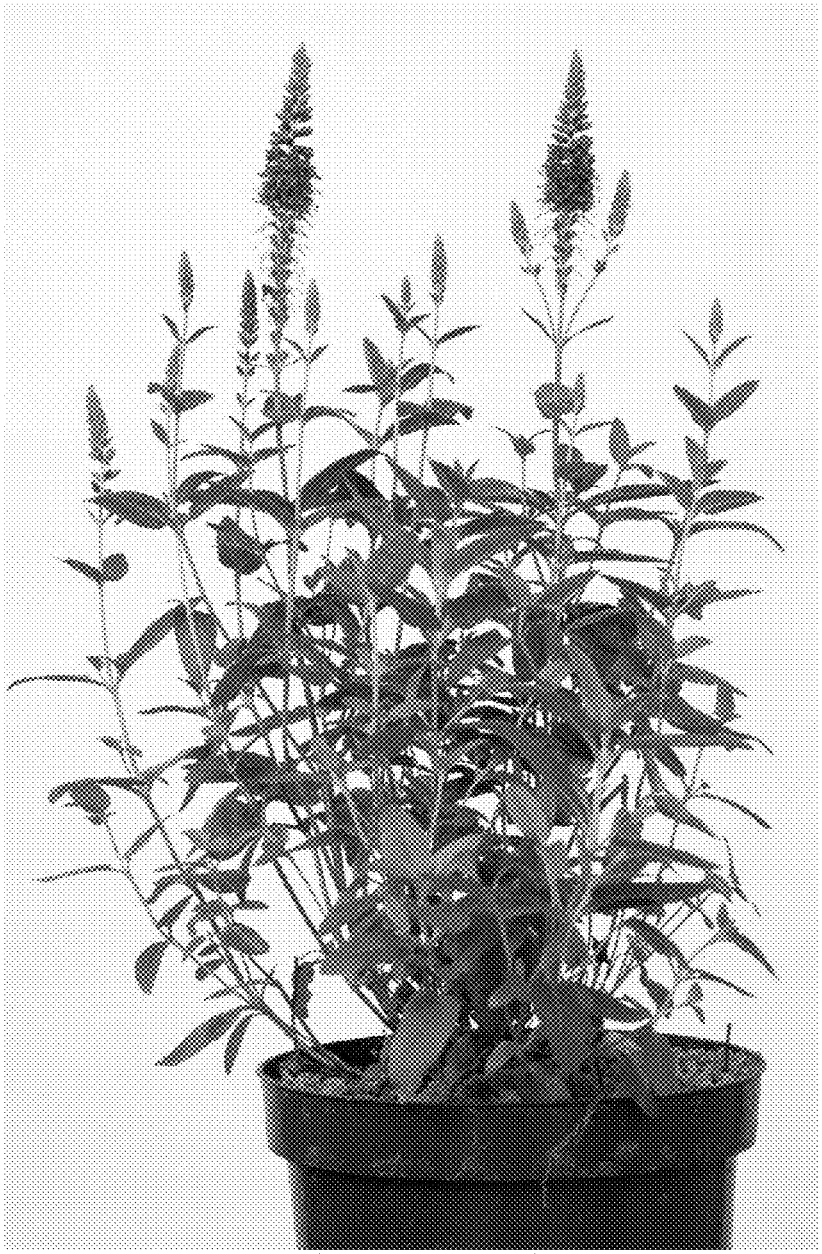

Botanical designation: *Veronica longifolia* X *Veronica spicata.*

Cultivar denomination: 'ALLVBABY'.

STATEMENT REGARDING PRIOR DISCLOSURES BY THE INVENTOR/APPLICANT & ASSIGNEE

An European Community Plant Breeder's Rights application for the instant plant was filed by the Assignee, Allplants Holding B.V. of Cuijk, The Netherlands on Jun. 15, 2021, application number 2021/1603. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Veronica* plant, botanically known as *Veronica longifolia* X *Veronica spicata*, typically grown as a garden plant and hereinafter referred to by the name 'Allvbaby'.

The new *Veronica* plant is a product of a planned breeding program conducted by the Inventor in Rijswijk, The Netherlands. The objective of the breeding program is to create new attractive *Veronica* plants with attractive flowers and good garden performance.

The new *Veronica* plant originated from an open-pollination in June, 2019 of *Veronica longifolia* X *Veronica spicata*

'Allvglove', disclosed in U.S. Plant Pat. No. 28,798, as the female, or seed, parent with an unknown selection of *Veronica longifolia* X *Veronica spicata* as the male, or pollen, parent. The new *Veronica* plant was discovered and selected by the Inventor as a single flowering plant from within the progeny of the stated open-pollination in a controlled nursery environment in Rijswijk, The Netherlands in July, 2020.

Asexual reproduction of the new *Veronica* plant by terminal stein cuttings in a controlled environment in Rijswijk, The Netherlands, since July, 2020 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allvbaby'. These characteristics in combination distinguish 'Allvbaby' as a new and distinct *Veronica* plant:

1. Relatively compact and broadly upright plant habit.
2. Moderately vigorous growth habit.
3. Freely branching habit.
4. Medium green-colored leaves.
5. Freely flowering habit.
6. Dense inflorescences with numerous violet-colored flowers.
7. Good performance as a garden plant.

Plants of the new *Veronica* differ primarily from plants of the female parent, 'Allvglove', primarily in plant habit as plants of the new *Veronica* are more compact than plants of 'Allvglove'.

Plants of the new *Veronica* can be compared to plants of *Veronica longifolia* 'Allsurprise', not patented. In side-by-side comparisons, plants of the new *Veronica* differ primarily from plants of 'Allsurprise' in the following characteristics:

1. Plants of the new *Veronica* are more compact than plants of 'Allsurprise'.
2. Plants of the new *Veronica* have narrower and more symmetrical inflorescences than plants of 'Allsurprise'.
3. Flowers of plants of the new *Veronica* are violet in color whereas flowers of plants of 'Allsurprise' are dark blue in color.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet (FIG. 1) comprises a side perspective view of a typical flowering plant of 'Allvbaby' grown in a container.

Figure 3:
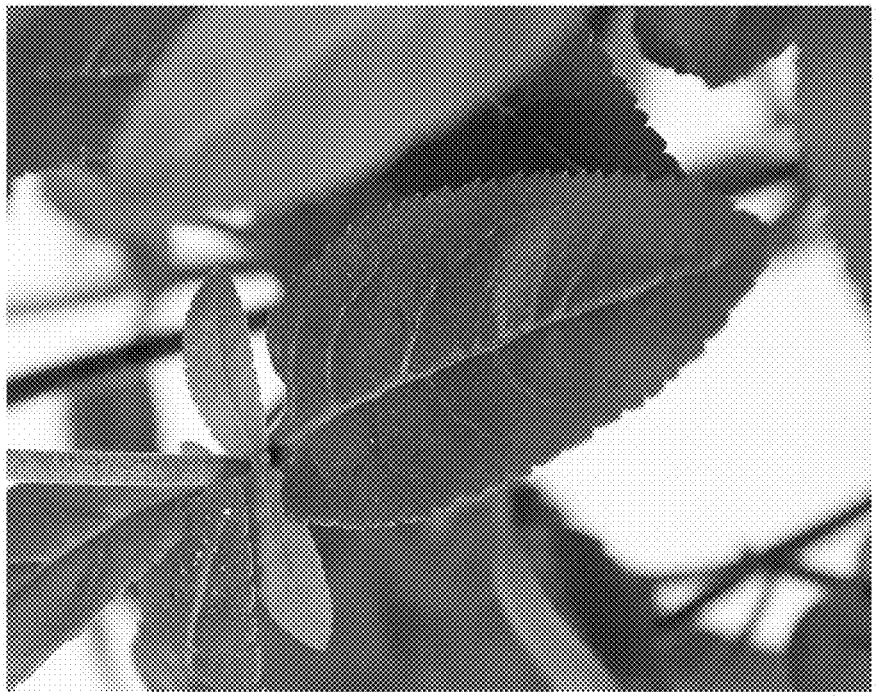
Figure 2:
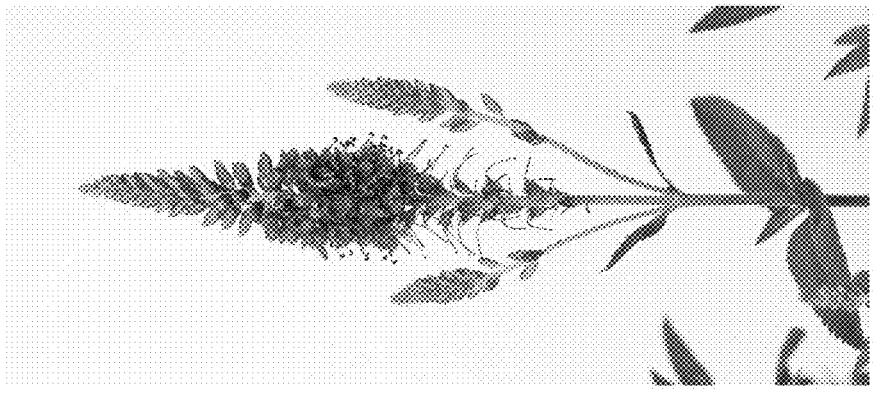

The photographs on the second sheet are close-up views of typical inflorescences (FIG. 2) and typical leaves (FIG. 3) of 'Allvbaby'.

DETAILED BOTANICAL DESCRIPTION

Plants used for the aforementioned photographs and following description were grown in ground beds and in 15-cm containers during the summer in a outdoor nursery in Rijswijk, The Netherlands and under cultural practices typical of commercial *Veronica* production. During the production of the plants, day temperatures ranged from 15° C. to 30° C. and night temperatures ranged from 6° C. to 18° C. Plants were four months old when the photographs and the description were taken. In the following description, color references are made to The Royal Horticultural Society Colour Chart, 2015 Edition, except where general terms of ordinary dictionary significance are used.

Botanical classification: *Veronica longifolia* X *Veronica spicata* 'Allvbaby'.

Parentage:

*Female, or seed, parent.*—*Veronica longifolia* X *Veronica spicata* 'Allvglove', disclosed as U.S. Plant Pat. No. 28,798.

*Male, or pollen, parent.*—Unknown selection of *Veronica longifolia* X *Veronica spicata*, not patented.

Propagation:

*Type cutting.*—Terminal stein cuttings.

*Time to initiate roots, summer.*—About 7 to 14 days at temperatures ranging from 12° C. to 30° C.

*Time to produce a rooted young plant, summer.*—About 28 to 32 days at temperatures ranging from 12° C. to 30° C.

*Root description.*—Fine, fleshy; typically white in color, actual color of the roots is dependent on substrate composition, water quality, fertilizer type and formulation, substrate temperature and physiological age of roots.

*Rooting habit.*—Freely branching; dense.

Plant description:

*Plant type.*—Herbaceous perennial.

*Plant and growth habit.*—Relatively compact and broadly upright plant habit with dense inflorescences; overall plant shape, broadly ovate; moderately vigorous growth habit and low to moderate growth rate.

*Plant height, soil level to top of foliar plane.*—About 23.8 cm.

*Plant height, soil level to top of floral plane.*—About 33.7 cm.

*Plant width.*—About 28.7 cm.

*Lateral branch description.*—Branching habit: Freely branching habit with about ten basal stems, each with about six secondary branches; pinching will enhance lateral branching. Length (excluding inflorescence): About 12.6 cm. Diameter: About 1.5 mm. Internode length: About 3.7 cm. Strength: Strong. Aspect: Erect to about 50° from vertical. Texture and luster: Densely pubescent; slightly glossy. Color, developing: Close to 145B. Color, developed: Close to 146D.

Leaf description:

*Arrangement.*—Opposite or in whorls of three, simple.

*Length.*—About 4.2 cm.

*Width.*—About 2.1 cm.

*Shape.*—Narrowly ovate; slightly carinate.

*Apex.*—Broadly acute.

*Base.*—Truncate to short attenuate.

*Margin.*—Crenate to serrate; not lobed.

*Texture and luster, upper surface.*—Moderately pubescent; not rugose; slightly glossy.

*Texture and luster, lower surface.*—Sparsely pubescent with exception of midvein which is densely pubescent; not rugose; slightly glossy.

*Venation pattern.*—Pinnate.

*Color.*—Developing leaves, upper surface: Close to 143A. Developing leaves, lower surface: Close to 146B. Fully expanded leaves, upper surface: Slightly darker than between 137B and 143A; venation, close to 144B. Fully expanded leaves, lower surface: Close to 147B; venation, close to 146D.

*Petioles.*—Length: About 8 mm. Diameter: About 1 mm by 1.5 mm. Strength: Strong. Texture and luster, upper surface: Moderately pubescent; moderately glossy. Texture and luster, lower surface: Moderately pubescent; slightly glossy. Color, upper surface: Close to 144A. Color, lower surface: Close to 144B; margins, close to 143B.

Flower description:

*Flower arrangement and shape.*—Single campanulate flowers arranged on dense terminal racemes; flowers face mostly outwardly.

*Flowering habit.*—Freely flowering habit with about 275 flowers developing per inflorescence and about 3,850 flowers developing per plant during the flowering season.

*Fragrance.*—None detected.

*Natural flowering season.*—Long flowering period; plants flower continuously from the summer until the autumn in The Netherlands; plants begin flowering about 13 weeks after planting.

*Flower longevity.*—Individual flowers last about seven days and inflorescences last about 20 days on the plant; flowers not persistent.

*Flower buds.*—Length: About 5 mm. Diameter: About 2 mm. Shape: Narrowly ovate. Texture and luster: Smooth, glabrous; matte. Color: Close to N82A; developing calyx, close to 138B.

*Inflorescence height* (*length*).—About 9.2 cm.

*Inflorescence diameter.*—About 2.3 cm.

*Flower diameter.*—About 7 mm by 8 mm.

*Flower height.*—About 9 mm.

*Throat diameter.*—About 3 mm.

*Tube length.*—About 3 mm.

*Tube diameter.*—About 3 mm.

*Petals.*—Quantity and arrangement: Four in a single whorl; upper and lateral petals broader than the lower petal; petals fused about 50% of the petal length from the base. Length, all petals: About 6 mm. Width, upper and lateral petals: About 3 mm. Width, lower petal: About 2 mm. Shape, upper and lateral petals: Obovate; slightly concave. Shape, lower petal: Oblong; slightly concave. Apex, all petals: Obtuse. Margin, all petals: Entire; not undulate. Texture and luster, all petals, upper and lower surfaces: Smooth, glabrous; matte. Texture and luster, throat: Smooth, glabrous; matte. Texture and luster, tube: Densely pubescent; matte. Color, all petals: When opening, upper surface: Close to N88B. When opening, lower surface: Close to N82A. Fully opened, upper surface: Close to 86B; venation, close to 86B; color does not change with subsequent development. Fully opened, lower surface: Close to N87A; venation, close to N87A; color does not change with subsequent development. Throat: Close to 86B; venation, close to 86B. Tube: Close to N88C; venation, close to 86B.

*Sepals.*—Quantity and arrangement: Four arranged in a single whorl and fused at the base. Length: About 2 mm to 2.5 mm. Width: About 1 mm to 1.25 mm. Shape: Ovate to narrowly ovate. Apex: Acute. Base: Broadly cuneate, fused. Margin: Entire. Texture and luster, upper and lower surfaces: Smooth, glabrous; matte. Color: When opening, upper and lower surfaces: Close to 138B. Fully opened, upper and lower surfaces: Close to 138B.

*Peduncles.*—Length: Primary peduncles, about 8.9 cm; secondary peduncles, about 5.8 cm. Diameter: About 2 mm. Aspect: Upright; secondary peduncles, about 20° from main peduncle axis. Strength: Strong. Texture and luster: Densely pubescent; slightly glossy. Color: Close to 144B.

*Pedicels.*—Length: About 1.25 mm. Diameter: About 0.5 mm. Aspect: About 60° from peduncle axis. Strength: Moderately strong; flexible. Texture and luster: Densely pubescent; slightly glossy. Color: Close to 177B.

*Flower bracts.*—None observed.

*Reproductive organs.*—Stamens: Quantity per flower: Two. Filament length: About 5.5 mm. Filament color: Close to 86B. Anther size: About 0.75 mm by 2 mm. Anther shape: Oblong; dorsifixed. Anther color: Close to N77B. Pollen amount: Moderate. Pollen color: Close to 156A. Pistils: Quantity per flower: One. Pistil length: About 7 mm. Stigma diameter: About 2 mm. Stigma shape: Club-shaped. Stigma color: Close to N92A. Style length: About 6.75 mm. Style color: Close to N88A; towards the proximal end, close to N88C. Ovary color: Close to 145B.

*Seeds and fruits.*—To date, seed and fruit development has not been observed on plants of the new *Veronica*.

Pathogen & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, temperatures ranging from about −29° C. to about 35° C. and to be suitable for USDA Hardiness Zones 4 through 9.

It is claimed:

1. A new and distinct *Veronica* plant named 'Allvbaby' as illustrated and described.

* * * * *